United States Patent
Wilmink et al.

(10) Patent No.: US 11,463,803 B2
(45) Date of Patent: Oct. 4, 2022

(54) ACOUSTIC DEVICE WITH DEFORMABLE SHAPE AS VALVE

(71) Applicant: Sonova AG, Staefa (CH)

(72) Inventors: Engbert Wilmink, Delft (NL); Nishant Shankar Lawand, Delft (NL); Krisztian Kepiro, Bekescsaba (HU)

(73) Assignee: Sonova AG, Staefa (CH)

( * ) Notice: Subject to any disclaimer, the term of this patent is extended or adjusted under 35 U.S.C. 154(b) by 0 days.

(21) Appl. No.: 17/148,812

(22) Filed: Jan. 14, 2021

(65) Prior Publication Data
US 2021/0227315 A1  Jul. 22, 2021

(30) Foreign Application Priority Data
Jan. 22, 2020  (NL) ................................... 2024731

(51) Int. Cl.
*H04R 1/10*  (2006.01)
*H04R 1/28*  (2006.01)

(52) U.S. Cl.
CPC ......... *H04R 1/2823* (2013.01); *H04R 1/1016* (2013.01); *H04R 1/1041* (2013.01)

(58) Field of Classification Search
CPC .. H04R 1/2826; H04R 1/2846; H04R 1/2849; H04R 2460/11; H04R 1/2823; F16K 7/00; F16K 7/10; F16K 7/20; F16K 31/06; F16K 31/082
See application file for complete search history.

(56) References Cited

U.S. PATENT DOCUMENTS

| | | | | |
|---|---|---|---|---|
| 2,786,898 A * | 3/1957 | Schultz | ............... | H04R 21/028 369/150 |
| 3,702,123 A * | 11/1972 | Macken et al. | ...... | H04R 25/652 181/135 |
| 4,056,255 A * | 11/1977 | Lace | ..................... | F16K 31/082 251/129.15 |
| 4,845,688 A * | 7/1989 | Butler | .................... | G10K 9/121 367/174 |
| 5,285,805 A * | 2/1994 | Proper | ..................... | F16K 7/20 137/1 |

(Continued)

FOREIGN PATENT DOCUMENTS

| | | | | |
|---|---|---|---|---|
| DE | 2201560 A1 * | 7/1973 | ............... | F16K 7/20 |
| EP | 2941018 A1 | 11/2015 | | |

(Continued)

OTHER PUBLICATIONS

European Patent Office, Dutch Search Report and Written Opinion in corresponding Netherlands Application No. 2024731, dated Jul. 27, 2020 (9 pages).

*Primary Examiner* — Ryan Robinson
(74) *Attorney, Agent, or Firm* — Leydig, Voit & Mayer, Ltd.

(57) ABSTRACT

An acoustic device is described that comprises an acoustic channel extending through its housing and an acoustic valve disposed in the acoustic channel. The acoustic valve is configured to determine a passage of sound through the housing via the acoustic channel. The acoustic valve comprises a deformable shape forming a deformable perimeter of the acoustic channel, and an actuating mechanism configured to exert an actuating force deforming the deformable shape causing the deformable perimeter to move and change the passage of sound.

16 Claims, 14 Drawing Sheets

(56) References Cited

U.S. PATENT DOCUMENTS

| | | | | |
|---|---|---|---|---|
| 6,950,373 B2* | 9/2005 | Butler | ............ | H04R 1/44 |
| | | | | 310/320 |
| 7,338,029 B2* | 3/2008 | Asai | ............ | F16K 7/14 |
| | | | | 251/129.15 |
| 8,090,134 B2* | 1/2012 | Takigawa | ............ | H04R 1/345 |
| | | | | 381/373 |
| 8,798,304 B2* | 8/2014 | Miller | ............ | H04R 1/326 |
| | | | | 381/356 |
| 8,923,543 B2* | 12/2014 | Sacha | ............ | H04R 25/652 |
| | | | | 381/324 |
| 9,033,307 B2* | 5/2015 | Friedrich | ............ | F16K 99/0001 |
| | | | | 251/61.1 |
| 9,185,480 B2* | 11/2015 | Howes | ............ | H04R 1/086 |
| 9,208,769 B2* | 12/2015 | Azmi | ............ | G10K 11/17885 |
| 9,357,283 B2* | 5/2016 | Darlington | ............ | H04R 1/1016 |
| 9,621,979 B2* | 4/2017 | Bakalos | ............ | H04R 5/033 |
| 9,860,660 B1* | 1/2018 | Bosscher | ............ | H04R 3/007 |
| 10,036,478 B2* | 7/2018 | Katsuda | ............ | F16K 15/147 |
| 10,567,866 B1* | 2/2020 | Liang | ............ | H04R 9/06 |
| 10,582,303 B2* | 3/2020 | van Halteren | ............ | H04R 11/02 |
| 10,687,153 B2* | 6/2020 | Albahri | ............ | H04R 25/407 |
| 10,805,746 B2* | 10/2020 | Bolsman | ............ | H04R 25/65 |
| 10,869,119 B2* | 12/2020 | Lawand | ............ | H04R 1/2857 |
| 10,932,069 B2* | 2/2021 | Jones | ............ | H04R 1/1041 |
| 10,945,084 B2* | 3/2021 | Lawand | ............ | H04R 1/1041 |
| 11,102,576 B2* | 8/2021 | Miller | ............ | H04R 1/1016 |
| 2016/0127818 A1 | 5/2016 | Ambrose | | |
| 2016/0150310 A1 | 5/2016 | Bakalos | | |
| 2016/0255433 A1 | 9/2016 | Grinker | | |
| 2017/0251292 A1* | 8/2017 | Wiederholtz | ............ | H04R 1/1016 |
| 2019/0074423 A1* | 3/2019 | Hodgins | ............ | H01L 41/0536 |
| 2019/0106416 A1 | 4/2019 | Puentener et al. | | |
| 2019/0106436 A1 | 4/2019 | Chakravarty et al. | | |
| 2019/0106438 A1 | 4/2019 | Eary et al. | | |
| 2019/0208301 A1* | 7/2019 | Monti | ............ | H04R 25/652 |
| 2019/0320272 A1 | 10/2019 | Jones et al. | | |
| 2020/0178003 A1* | 6/2020 | Zurbruegg | ............ | H04R 25/603 |
| 2020/0260197 A1* | 8/2020 | Thomsen | ............ | H04R 1/1041 |
| 2020/0352788 A1* | 11/2020 | Van 'T Hof | ............ | H04R 25/658 |

FOREIGN PATENT DOCUMENTS

| | | | | |
|---|---|---|---|---|
| EP | 3169290 B1 | 5/2017 | | |
| EP | 3541090 A1 * | 9/2019 | ............ | F16K 24/00 |
| GB | 457213 A * | 11/1936 | ............ | H04R 1/42 |
| WO | WO 2008/086188 A1 | 7/2008 | | |
| WO | WO-2020101491 A1 * | 5/2020 | ............ | H04R 25/456 |
| WO | WO-2021156333 A1 * | 8/2021 | ............ | F16K 7/00 |

\* cited by examiner

ACOUSTIC DEVICE WITH DEFORMABLE SHAPE AS VALVE

CROSS-REFERENCE TO RELATED APPLICATIONS

This patent application claims priority to Netherlands Application No. 2024731, filed Jan. 22, 2020, the contents of which are expressly incorporated by reference in their entirety, including any references contained therein.

TECHNICAL FIELD AND BACKGROUND

The present disclosure relates to an acoustic device and method of controlling the device.

In the field of hearing and audio, various acoustic devices exist that can be used, e.g., to protect, enhance and/or enable users to have a normal or better hearing experience. Examples of such acoustic devices may include hearing protection devices, hearing instruments, hearing aids, hearables, et cetera. Depending on the type, the acoustic devices can be placed at different positions in and around the human ear/canal. For example, acoustic devices can take the form of ear buds or head phones.

Typically, an acoustic device comprises one or more channels that can be used to form a connection between the ear canal and external surroundings. In some cases, the channel may help to prevent a feeling of occlusion, e.g. by allowing sound to travel from the ear drum to the external environment or vice versa. In other or further cases, the channel may act as a vent, e.g. to provide ventilation inside the ear canal and/or relieve static pressure in the ear canal.

An acoustic valve can be used to control the sound or air passing in and out of the system. For example, the valve can be installed in the channel or vent. In some cases, the acoustic valve can be switched between different states, e.g. based on one or more control parameters or other conditions. For example, an open state can be uses in situations where the natural sound (including directionality) is preserved thus getting rid of the occlusion to a certain extent by allowing sound to escape from the ear canal. It allows free flow of ear, hence offering ventilation and occlusion reduction. For example, a closed state provides a seal from the external environment to create an enhanced sound quality (in comparison with the open state) for low frequencies from the sound source (for e.g. Balanced Armature Receivers or Dynamic drivers). In addition to this, directionality and noise suppression can also be achieved in this state.

As background, various types of acoustic devices, channels, and valves are described, e.g., in U.S. Pat. No. 8,798,304B2, WO2008/086188A1, U.S. Pat. No. 8,923,543B2, WO2011149970A1, US20160255433A1, US20190106416A1, US20190106436A1, US20190106438A1, EP3169290B1, US20190320272A1. For example, US 20190320272A1 describes acoustic valves that include a housing having an acoustic inlet, an acoustic outlet, and an acoustic passage between the inlet and the outlet. An electrical coil is disposed in the housing and configured to generate a magnetic field when energized by an actuation signal. A spring is coupled to an armature movably disposed in the housing between a first surface and a second surface. The valve has a first stable state wherein the armature is positioned against one surface when the electrical coil is not energized, and the valve has a second stable state wherein the armature is positioned against the other surface when the electrical coil is not energized. The armature is movable between the first and second states when the electrical coil is energized, wherein the acoustic passage is more obstructed when the armature is in one state than when the armature is in the other state.

There is a need for further improvement in an acoustic devices, in particular an acoustic valve that is both reliable and easy to switch.

SUMMARY OF THE INVENTION

Aspects of the present disclosure relate to an acoustic device comprising a housing; an acoustic channel extending through the housing; and an acoustic valve disposed in the acoustic channel and configured to determine a passage of sound through the housing via the acoustic channel. By using a deformable shape as part of the valve, a deformable perimeter of the acoustic channel can be formed. Accordingly, an actuating mechanism can be used to exert an actuating force deforming the deformable shape causing the deformable perimeter to move and change the passage of sound. Other or further aspects relate to a method of controlling the acoustic device. For example, the actuating mechanism can be energized to switch between a first state wherein the deformable shape blocks the acoustic channel to restrict the passage of sound; and a second state wherein the deformable shape clears the acoustic channel to allow the passage of sound.

BRIEF DESCRIPTION OF DRAWINGS

These and other features, aspects, and advantages of the apparatus, systems and methods of the present disclosure will become better understood from the following description, appended claims, and accompanying drawing wherein:

DETAILED DESCRIPTION

Figure 1A:
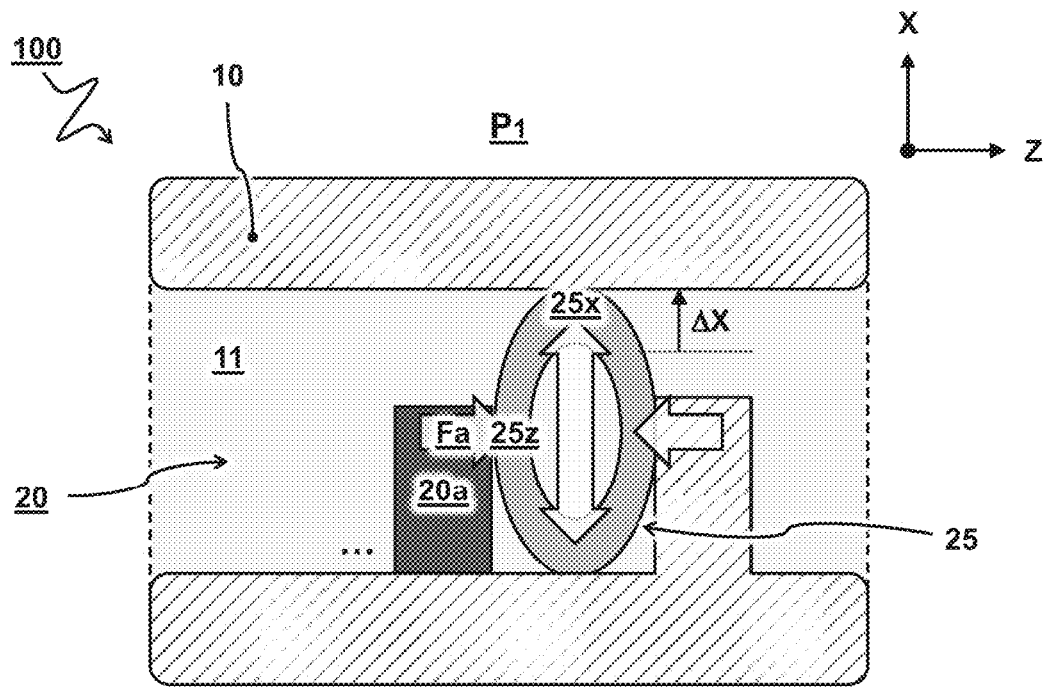
FIGS. 1A and 1B illustrate an acoustic device comprising a deformable shape and actuating mechanism to regulate the passage of sound in an acoustic channel of the housing.

Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise, it will be understood that when a connection between structures or components is described, this connection may be established directly or through intermediate structures or components unless specified otherwise.

The invention is described more fully hereinafter with reference to the accompanying drawings, in which embodiments of the invention are shown. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

Figure 1B:
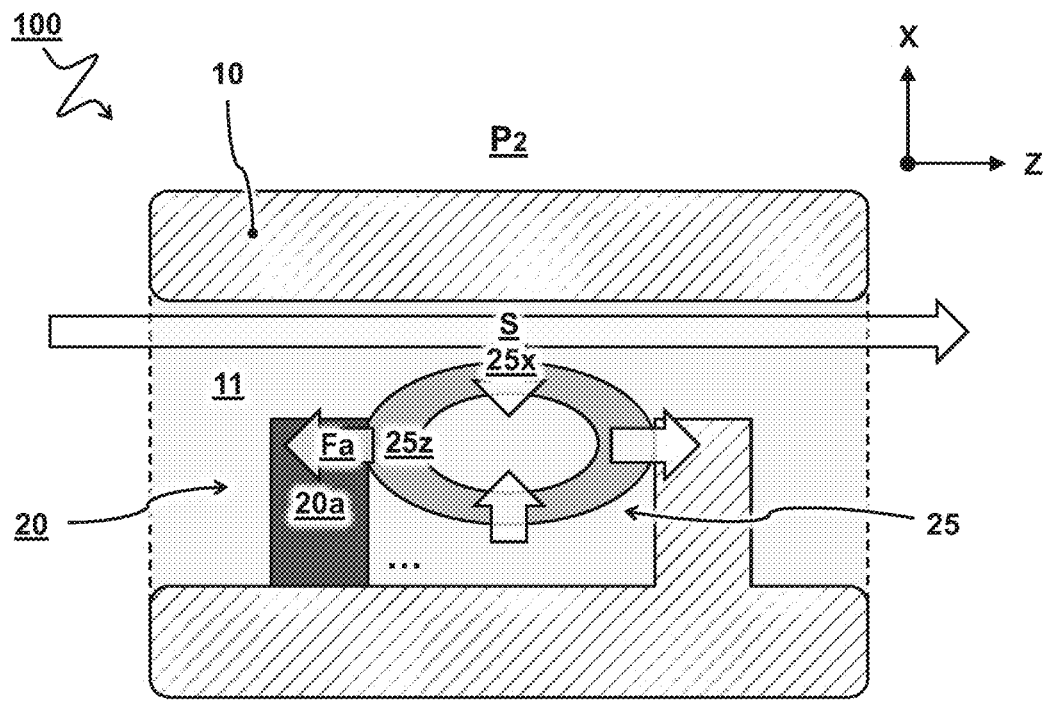

FIGS. 1A and 1B illustrate an acoustic device 100 comprising a deformable shape 25 and an actuating mechanism 20a to regulate the passage of sound S in an acoustic channel 11 of a housing 10.

In one embodiment, e.g. as shown, the acoustic device 100 comprises a housing 10 with an acoustic channel 11 extending through the housing 10. In another or further embodiment, an acoustic valve 20 is disposed in the acoustic channel 11 and configured to determine a passage of sound S through the housing 10 via the acoustic channel 11. In a preferred embodiment, the acoustic valve 20 comprises a deformable shape 25 forming a deformable perimeter 25x of the acoustic channel 11. In another or further preferred embodiment, an actuating mechanism 20a is configured to exert an actuating force Fa deforming the deformable shape 25 causing the deformable perimeter 25x to move ΔX and change the passage of sound S.

As the name implies, the deformable shape 25 is able to deform, or change its shape. Accordingly, the deformable shape 25 preferably comprises or essentially consists of deformable material. Preferably, the deformable shape 25 comprises a flexible material. The complementary concept of flexibility is stiffness, which is the extent to which an object resists deformation in response to an applied force. The more flexible the material is, the less stiff it is, i.e. the easier it is to deform. By deforming the shape, a perimeter or outer wall of the shape can also deform. In a particular illustrative example, the perimeter of the deformable shape 25 also forms a perimeter or wall bounding the acoustic channel 11. Accordingly, by moving the perimeter of the deformable shape 25, a wall of the acoustic channel 11 can also be moved that can affect the passage of sound S there through.

In an illustrative example, the actuating mechanism 20a is configured to change, by moving ΔX the deformable perimeter 25x in the acoustic channel 11, a state of the acoustic device 100 between at least a first state P1, wherein the passage of sound S is relatively restricted (or even closed), and a second state P2, wherein the passage of sound is relatively open. Also other or further states can be defined, e.g. one or more intermediate states allowing various degrees of attenuation. Alternatively, in addition to varying attenuation, the set of states may also include different filtering of sound, e.g. wherein a first state has a different sound transmission characteristic than a second state. For example, the moving deformable perimeter 25x can open or close different passages with different filters.

Preferably, the movement of the deformable perimeter 25x includes transverse movement ΔX substantially normal to a surface of the perimeter. Additionally, or alternatively, the movement may also include stretching and/or contracting of the deformable perimeter 25x. In an illustrative example, the actuating mechanism 20a is configured to exert the actuating force Fa on the deformable shape 25 causing the deformable perimeter 25x to expand into, or retract from, the acoustic channel 11 to thereby at least partially close (restrict), or open up (widen), the passage of sound S through the acoustic channel 11.

In one illustrative example, the actuating force Fa causes at least part of the deformable shape 25 to expand into the acoustic channel 11 that may partially or fully close off the channel in a first state P1 of the device. In another or further illustrative example, the actuating force Fa causes at least part of the deformable shape 25 to contract or retract from the passage, e.g. opening up an otherwise at least partially closed acoustic channel 11 in a second state P2 of the device.

In an illustrative example, the actuating mechanism 20a is configured to exert an actuating force Fa on the deformable shape 25 in a first direction Z causing the deformable shape 25 to deform in another, second direction X for changing the passage of sound S. As will become further apparent from the examples described herein, this can have various advantages such the closing of a relatively wide channel by relatively limited stroke of the actuator. Another or further advantage can be that the mechanism need not rely on an abutment surface at the end of its stroke. For example, the end of the stroke can be determined by a balancing of magnetic and resilient forces. In an advantageous illustrative example, the second direction X is transverse, or perpendicular, to the first direction Z.

In accordance with an illustrative example, the actuating mechanism 20a is configured to compress (or contract) the deformable shape 25 by exerting (or stop exerting e.g. in case of a resilient restoring force) the actuating force Fa in a first direction Z (e.g. axial direction) causing the deformable shape 25 to expand in another, second direction X (e.g. radial direction), wherein expansion of the deformable shape 25 in the second direction closes the acoustic channel 11 for at least partially blocking the passage of sound S.

In another or further illustrative example, the actuating mechanism 20a is configured to expand the deformable shape 25 in a first direction −Z causing the deformable shape 25 to compress in another, second direction −X. The expansion of the shape can also happen in multiple directions simultaneously (or sequentially), e.g. radially as in preferred embodiment described herein. In some illustrative examples, expansion closes the channel. In other or further examples, expansion opens the channel, e.g. by stretching a membrane as will be described later, e.g. with reference to FIGS. 11A-11C.

In an illustrative example, the deformable shape 25 comprises a flexible shell of deformable material. As will be appreciated, the actuating force Fa can be exerted on an actuated perimeter 25z of the deformable shape 25 indirectly causing the deformable perimeter 25x to move. For example, in the example shown, the actuating mechanism 20a is configured to exert the actuating force Fa on a proximal and/or distal side of the deformable shape 25 causing expansion and/or contraction on a lateral side of the shape. Here the lateral side forms the deformable perimeter 25x closing or opening the passage of sound S through the acoustic channel 11.

In some illustrative examples, a deformable shape with relatively high flexibility may be desired. For example, a hollow and/or relatively thin shell can more easily deform when a small actuating force Fa is applied. The shape can also be solid which may be more difficult to deform (higher stiffness). Deformation of the shell or other shape can be plastic and/or elastic, e.g. retaining, or recovering from, the deformation when the force is removed. In one example, a certain degree of stiffness or resilience may be desired, e.g. elastic stiffness or resilience that can provide a biasing or resilient force Fr resisting deformation (not indicated here). Additionally, or alternatively, the deformable shape 25 can be connected to a resilient element (not shown here) such as a spring that may augment or counter resilient properties of the deformable shape 25.

In an illustrative example, the deformable shape 25 is configured to recover a specific form in the absence of external forces. A temporary shape change that is self-reversing after the force or stress is removed, so that the object returns to its original shape, can be referred to as elastic deformation (e.g. as opposed to plastic deformation). In other words, elastic deformation may refer to a change in shape of a material that is recoverable after the force is removed. So the deformable shape advantageously comprises or essentially consists of a deformable material, most advantageously an elastically deformable material. For example, the deformable shape 25 comprises a resilient and/or elastic material such as rubber, or other similar material. The elastically deformable shape 25 may cause a resilient force that can help to restore its shape in some embodiments.

Figure 2A:
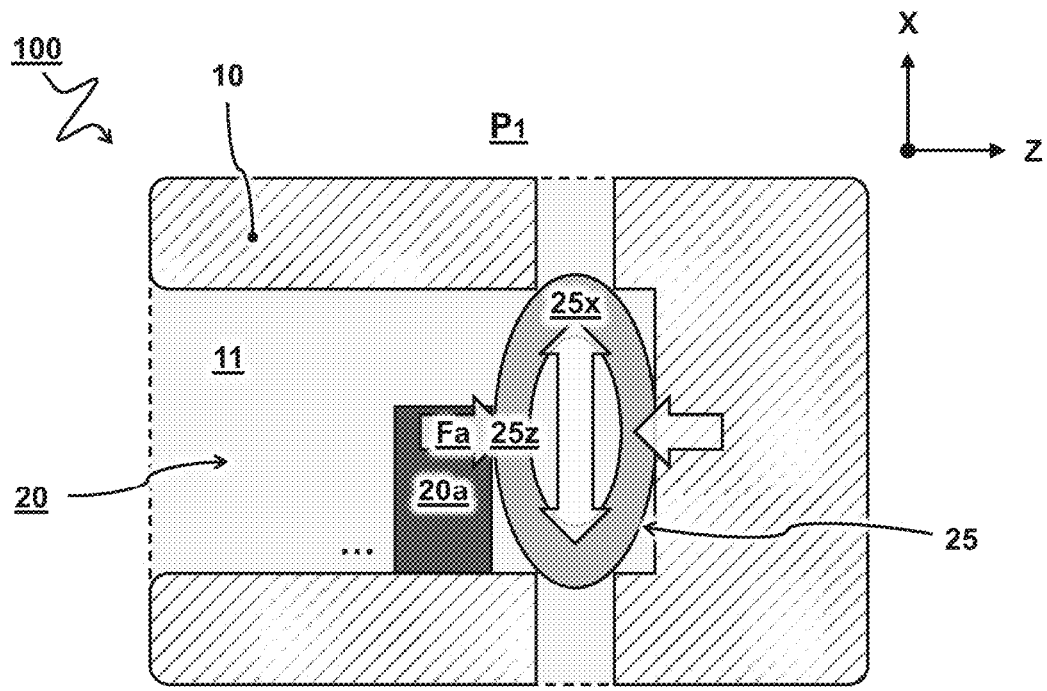
FIGS. 2A and 2B illustrate an acoustic device wherein the deformable shape is configured to open and close a side passage through the housing.
Figure 2B:
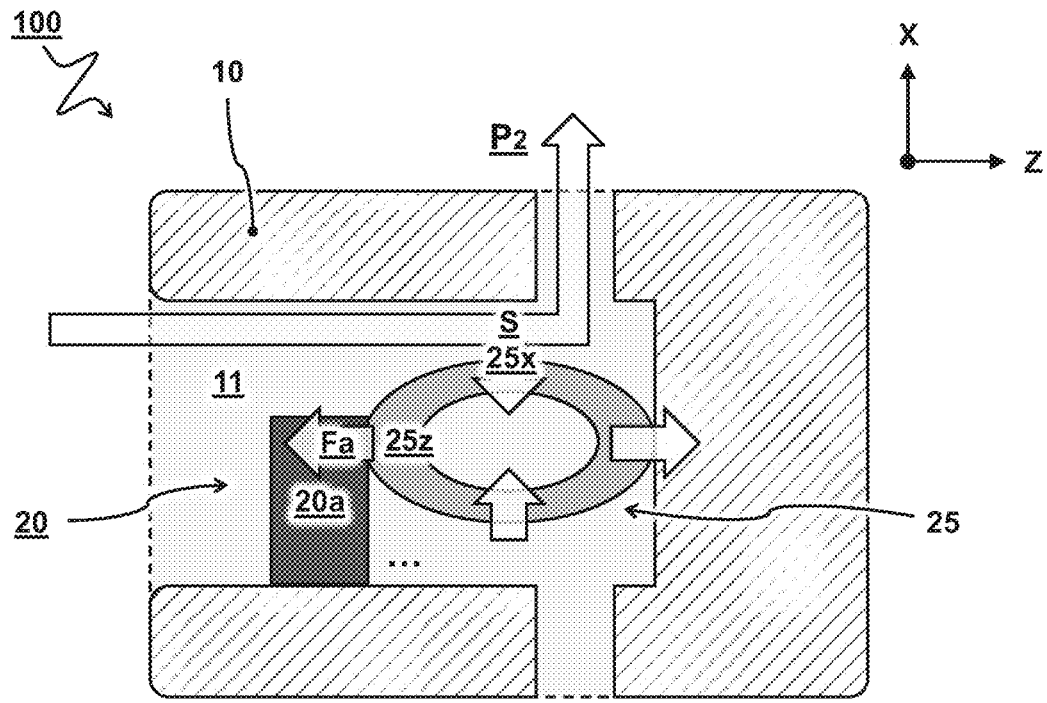

FIGS. 2A and 2B illustratively depict an acoustic device similar to FIGS. 1A and 1B, except the deformable shape 25 is configured to open and close a side passage through the housing 10.

Figure 3A:
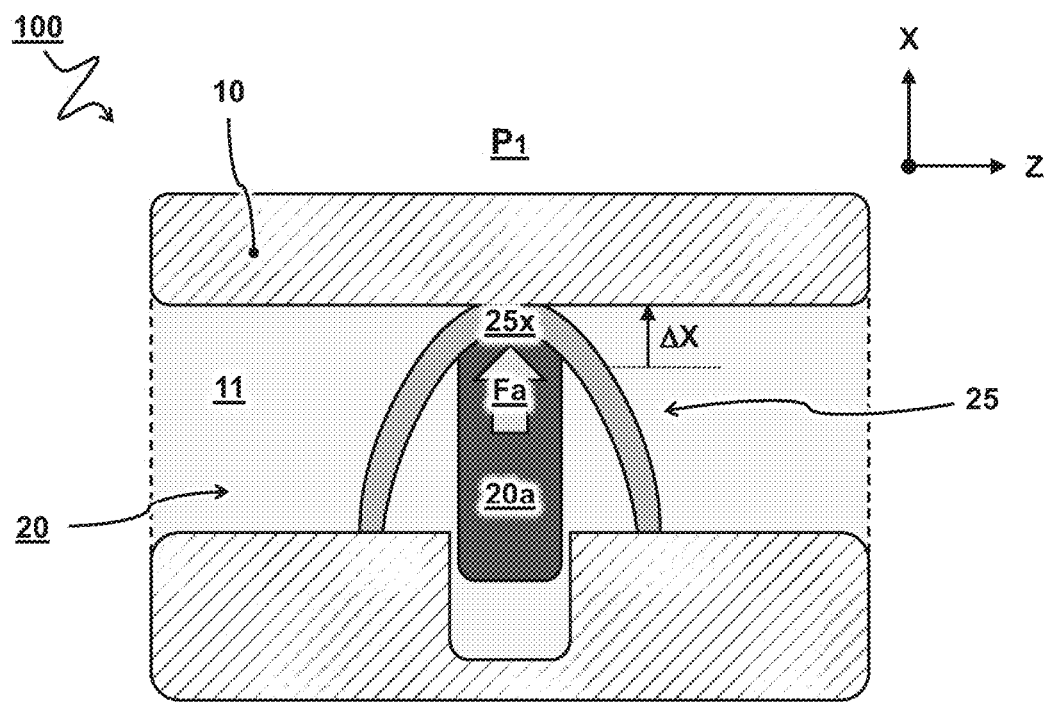
FIGS. 3A and 3B illustrate an acoustic device wherein the actuating mechanism is sealed from the acoustic channel inside the deformable shape.
Figure 3B:
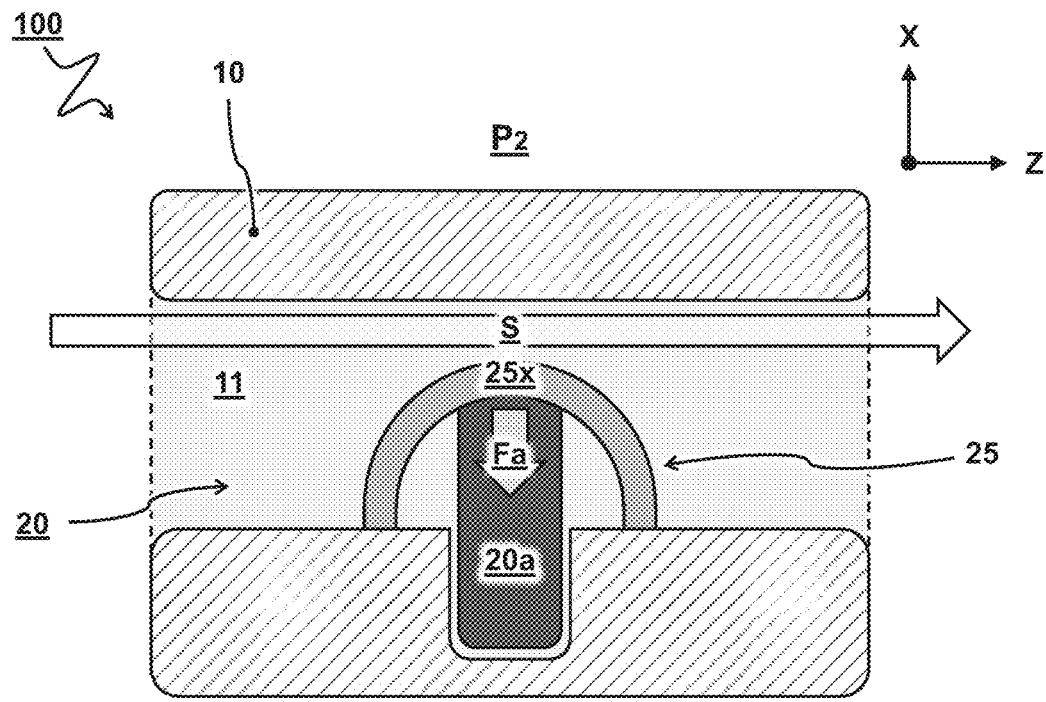

FIGS. 3A and 3B illustratively depict an acoustic device 100 wherein the actuating mechanism 20a is sealed from the acoustic channel 11 inside the deformable shape 25. In the device shown here, the actuating mechanism 20a is connected at a side of the deformable perimeter 25x to actuate in the same direction X as the movement ΔX of the perimeter. In other illustrative examples the directions can be different.

In an illustrative example, the deformable shape 25 is configured to form a barrier sealing the actuating mechanism 20a from an inside of the acoustic channel 11. Advantageously, the deformable shape 25 forms a shell, dome, and/or or bubble around the actuating mechanism 20a. As will be described in further detail later, the actuating mechanism 20a may comprise various components such as electric, magnetic, and/or mechanical (moving) components. By providing the deformable shape 25 as a barrier between the components of the actuating mechanism 20a and the inside of acoustic channel 11, it can be prevented or alleviated that pollutants such as ear wax or dust enter the acoustic channel and negatively affect the actuating mechanism 20a.

Figure 4A:
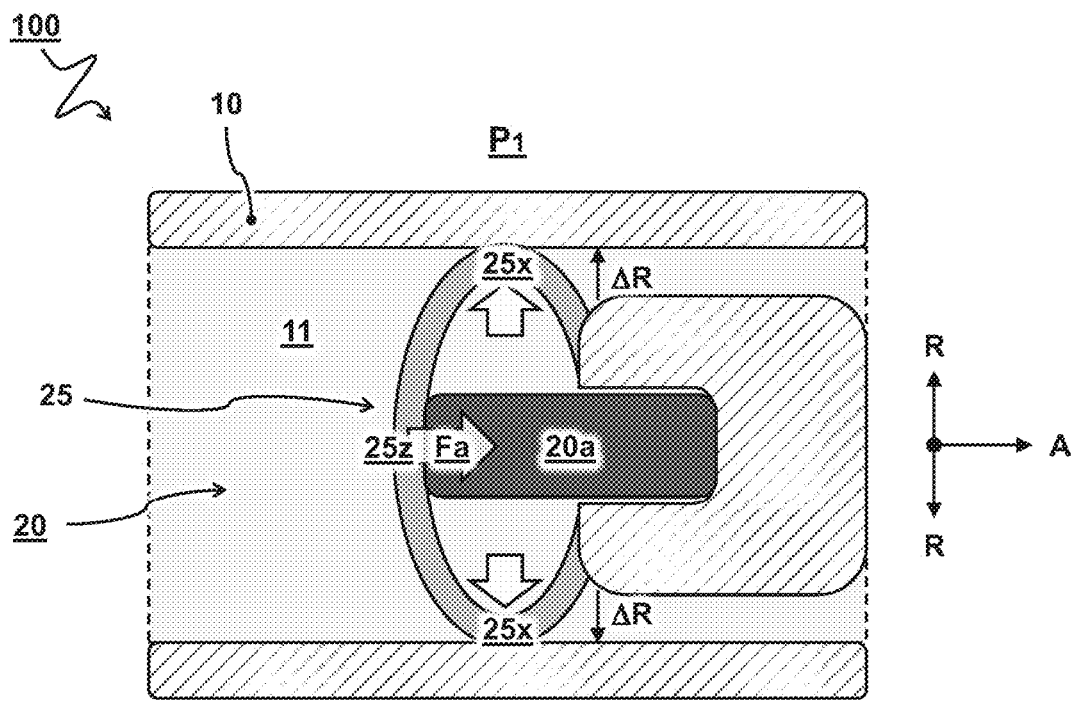
FIGS. 4A and 4B illustrate an acoustic device wherein the deformable shape is configured to radially expand and contract around an axially moving actuating mechanism.
Figure 4B:
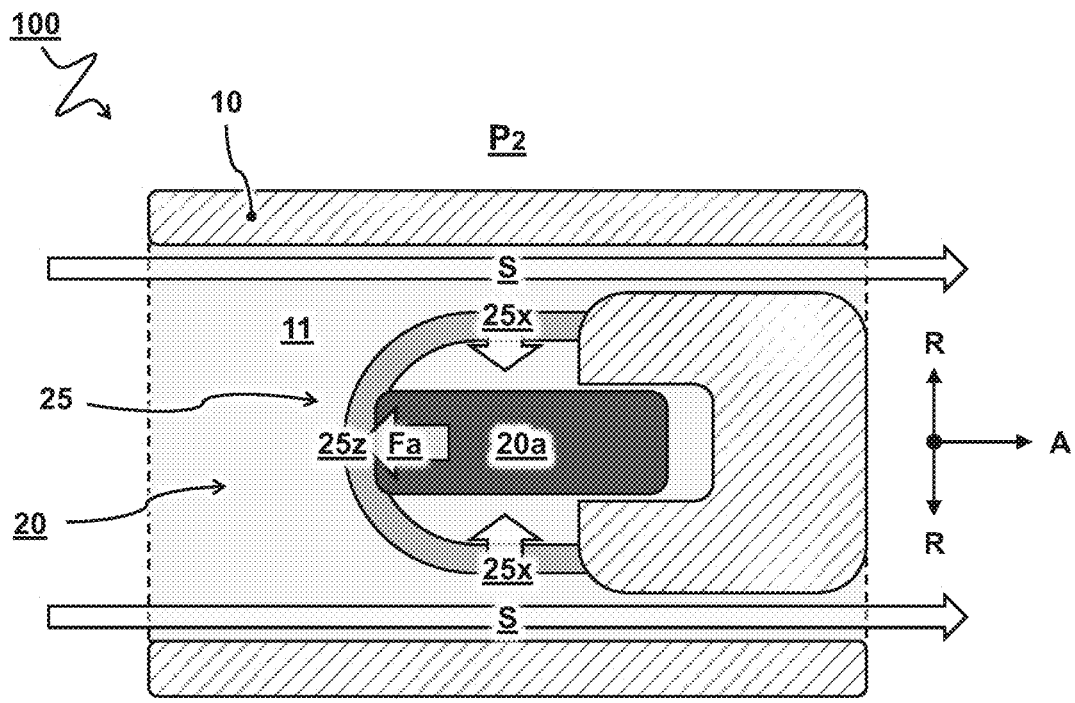

FIGS. 4A and 4B illustratively depict an acoustic device 100, wherein the deformable shape 25 is configured to radially expand and contract around an axially moving actuating mechanism 20a.

In an illustrative example, the actuating mechanism 20a is configured to exert the actuating force Fa in an axial direction A, causing the deformable shape 25 to expand or contract the deformable perimeter 25x in a radial direction R, around and transverse to the axial direction A. As shown, contraction or expansion ΔR in the radial direction R can be in multiple directions, which may including opposite directions, e.g. on opposite sides of the deformable shape 25.

In the following figures various examples are illustratively depicted wherein the actuating mechanism 20a comprises magnetic components such as magnetic pole pieces including a permanent magnet 21 and/or magnetizable material 24; and electromagnetic devices including an electromagnetic coil 22, and a yoke material 23.

Figure 5A:
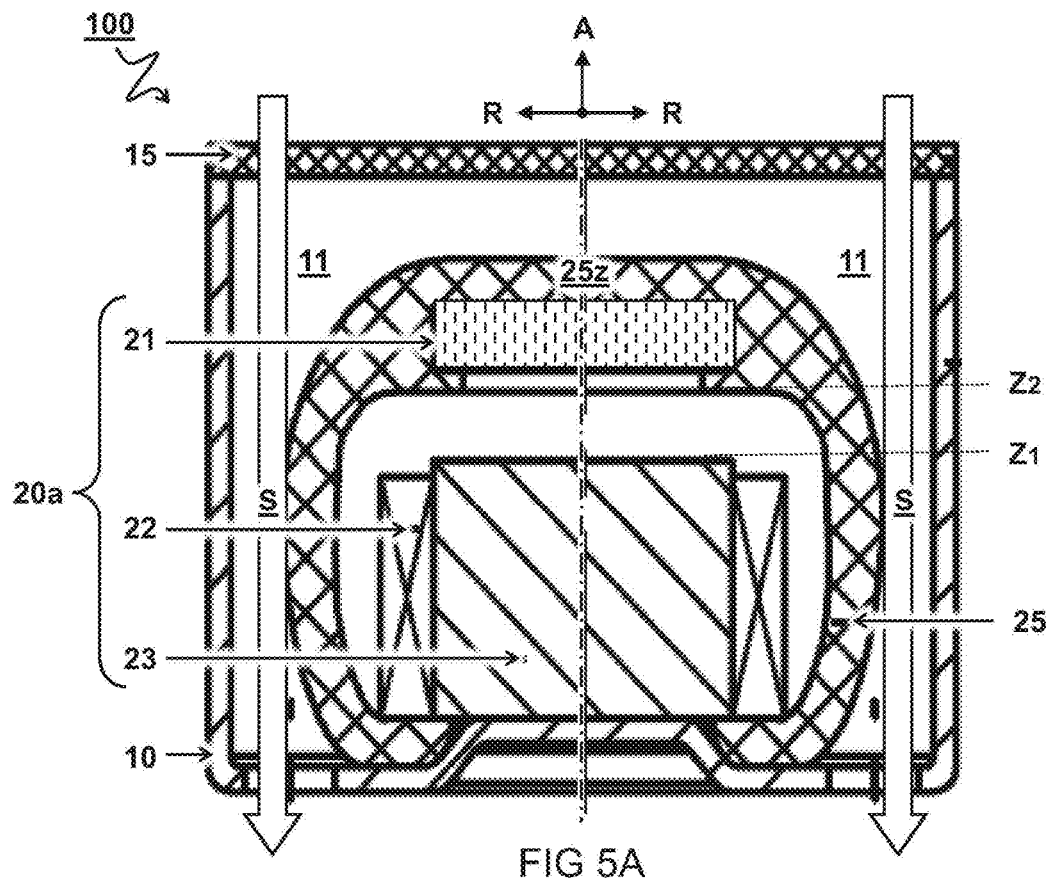
FIGS. 5A and 5B illustrate an acoustic device wherein the actuating mechanism comprises a moveable permanent magnet.
Figure 5B:
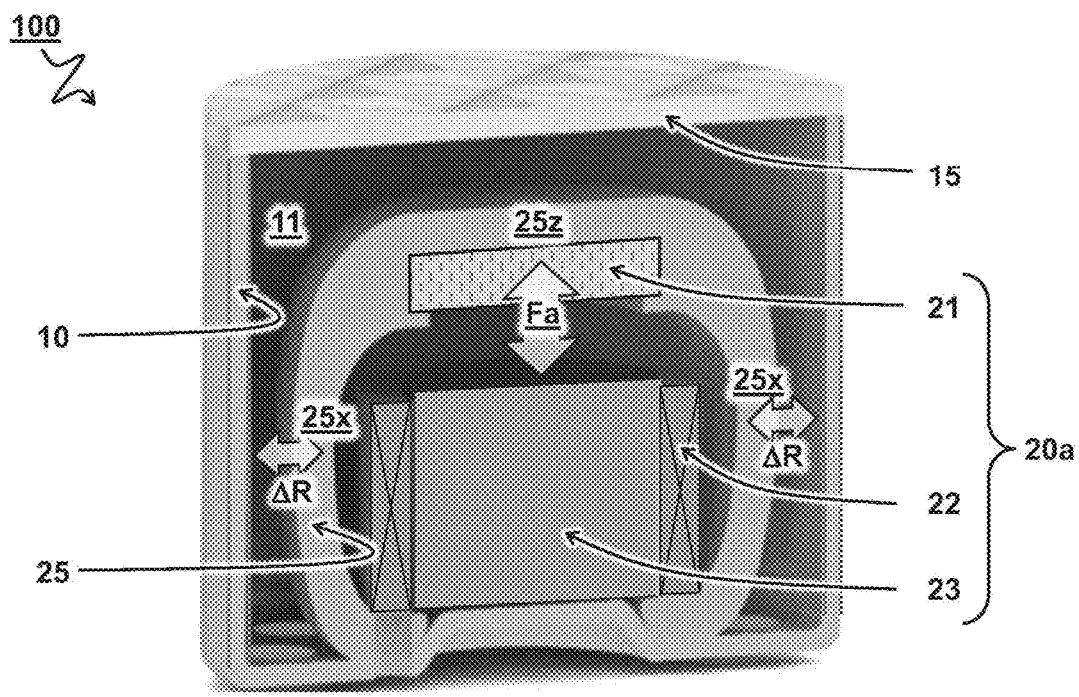

FIGS. 5A and 5B illustratively depict an acoustic device 100, wherein the actuating mechanism 20a comprises a moveable permanent magnet 21.

In illustrative examples, the actuating mechanism 20a comprises at least one permanent magnet 21. A permanent magnet can generate its own magnetic field in the absence of any external magnets or electrical currents. In some illustrative examples, the permanent magnet is configured to exert a magnetic force to keep parts of the acoustic device 100 attracted or repelled for maintaining a specific state, e.g. open or closed. In one illustrative example, e.g. as shown, the permanent magnet 21 is movable.

In an illustrative example, the actuating mechanism 20a comprises a moveable magnet 21 or magnetizable piece of material attached to a proximal side of the deformable shape 25. Advantageously, the permanent magnet 21 is at least partially embedded in the deformable material of the deformable shape 25. Typically, the deformable material is non-magnetic, e.g. having rubber-like properties. So by attaching, advantageously embedding, the magnetic material to a respective part of the deformable shape 25, the shape can be actuated by magnetic forces. An advantage of using a permanent magnet, e.g. having a specific field direction, may include the option to not only attract the material, but also repel (when magnetic field directions oppose each other).

In an illustrative example, the deformable shape 25 is rotation symmetric about an axial direction A. In some illustrative examples, the deformable shape 25 has at least a two-fold rotational symmetry. In other or further examples, the shape substantially has continuous rotational symmetry. For example, the deformable shape 25 forms a flexible round dome. Advantageously, the dome or other shape is disposed around the components of the actuating mechanism 20a, e.g. shielding the components from the inside of the acoustic channel 11.

In illustrative examples, e.g. as shown, the permanent magnet 21 is configured to move along an axial direction A, causing expansion or contraction of the deformable perimeter 25x in a radial direction R. For example, the permanent magnet 21 is attached to a proximal or distal side of the deformable shape 25 causing expansion/contraction in the radial direction R at a lateral side of the deformable shape 25. In the example shown, when the magnet 21 is moved along one direction of the axis A (here down), the walls of the deformable shape 25 forming the deformable perimeter 25x of the acoustic channel 11 are pushed outwards; and when the magnet 21 is moved along the other direction of the axis A (here up), the walls of the deformable shape 25 forming the deformable perimeter 25x of the acoustic channel 11 are pulled inwards.

In an illustrative example, the actuating mechanism 20a comprises an electromagnet 22, 23 to generate the actuating force Fa by generating a magnetic field acting on a moveable magnet 21 or magnetisable piece of material attached to the deformable shape 25. For example, the electromagnet comprises an electromagnetic coil 22 configured to generate a magnetic field depending on an electric current through the coil. For example, the magnetic field may depend on a magnitude and/or polarity of the current. Advantageously, the electromagnet 22, 23 also comprises a (magnetisable) yoke material 23 that can be disposed inside and/or outside the electromagnetic coil 22. The yoke material 23 can be used to guide the magnetic field that may enhance the attainable strength. In some embodiments, the yoke material 23 can be used to form a magnetic circuit through and around the electromagnetic coil 22, wherein a movable permanent magnet 21 or magnetisable material in the deformable shape 25 can complete the circuit and remain a relatively strong connection. For example, in the embodiment shown, the permanent magnet 21 can maintain a connection to the yoke material 23 at least when the distance there between is sufficiently low.

It will be appreciated that by using the deformable shape 25 exclusively around and outside the components of the actuating mechanism 20a (not between the components), the magnetic circuit can be relatively compact, which may improve magnetic field strength. For example, the magnetic field lines in principle do not need to cross any material that could obstruct the magnetic field lines. On the other hand, it can be advantageous in some cases to add a spacer between the movable magnet/material and the electromagnet so the magnetic force can limited.

In some illustrative examples, the actuating force Fa is generated only in one direction. For example, a resilient force of the deformable shape 25 or other resilient mechanism can act to restore the shape in the opposite direction. In an illustrative example, the electromagnet 22,23 is configured to selectively generate the actuating force Fa in each of at least two opposing direction, e.g. depending on a direction of current. For example, this may cause a displacement of the actuated perimeter 25z of the deformable shape 25, e.g. between a first position Z1 and a second position Z2. At the same time, the deformable perimeter 25x may also move over a respective distance ΔX In some illustrative examples, the acoustic channel 11 can form an open or half-open passage through the housing 10. In other or further embodiments, e.g. as shown, the housing 10 comprises at least one mesh 15, which may serve an acoustic function and/or shield an inside of the acoustic channel 11 from outside pollutants. Also other or further acoustic components can be included in or surrounding the acoustic channel 11 such as a membrane.

Figure 6A:
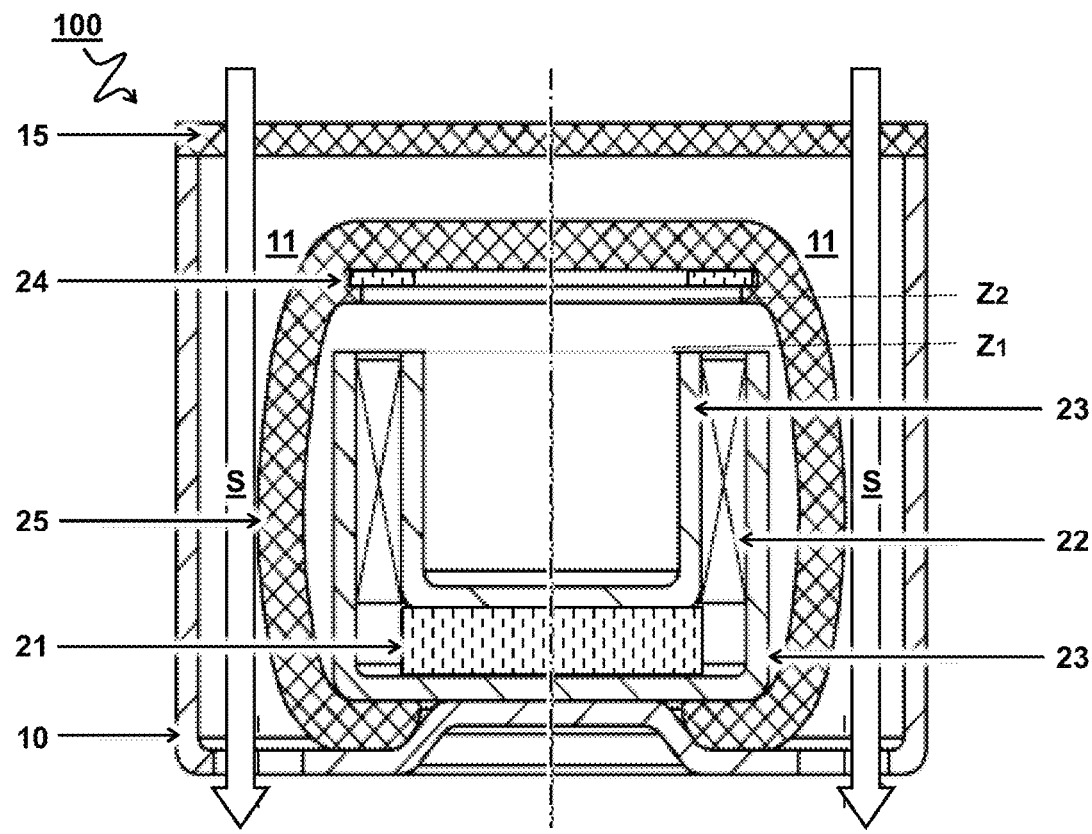
FIGS. 6A and 6B illustrate an acoustic device wherein the actuating mechanism comprises a stationary permanent magnet and moveable magnetisable material embedded in the deformable shape.
Figure 6B:
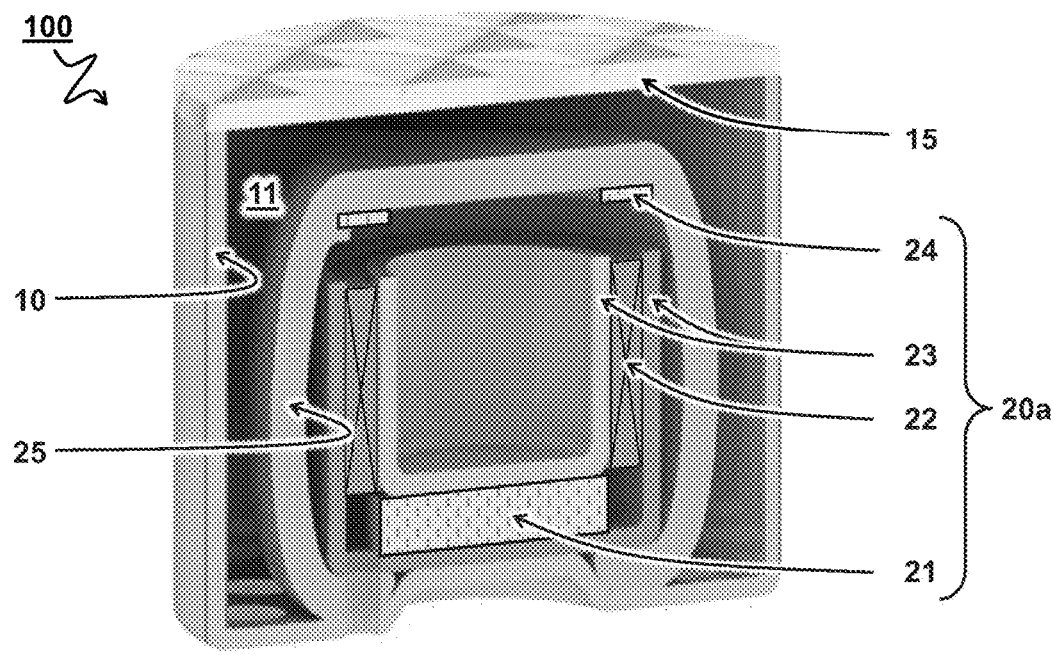

FIGS. 6A and 6B illustrate an acoustic device 100 wherein the actuating mechanism 20a comprises a stationary permanent magnet 21 and moveable magnetisable material 24 embedded in the deformable shape 25.

In an illustrative example, a stationary permanent magnet 21 is disposed between inner and outer yoke material 23 inside and outside an electromagnetic coil 22, wherein the magnetizable material 24 can complete the magnetic circuit and maintain the connection also in the absence of current through the electromagnetic coil 22. In one illustrative example, e.g. as shown, the yoke material 23 is shaped as a cup. For example, an inner cup of yoke material 23 is disposed concentrically inside the electromagnetic coil 22 and an outer cup of yoke material 23 is disposed concentrically outside the electromagnetic coil 22. In another or further example, e.g. as shown, the permanent magnet 21 is disposed between the bottoms of the inner and outer cups of yoke material 23. In some illustrative examples, e.g. as shown, the magnetizable material 24 is shaped as a ring. For example, the ring of magnetizable material 24 can complete a connection at between the top rims of the inner and outer cups of the yoke material 23.

By energizing the electromagnetic coil 22 the magnetic field of the permanent magnet extending through the yoke material 23 can be enhanced or counteracted. For example, this may cause the magnetizable material 24 to be attracted to or released from the yoke material 23. Optionally, the magnetizable material 24 may also be permanently magnetic, e.g. having an intrinsic magnetic field, which can increase the magnetic force and/or provide the option of repelling the magnetic material when using switching the electromagnetic coil 22 to produce a magnetic field with the same polarity as the magnetic field produced by the magnetic material facing the electromagnetic coil 22.

Figure 7A:
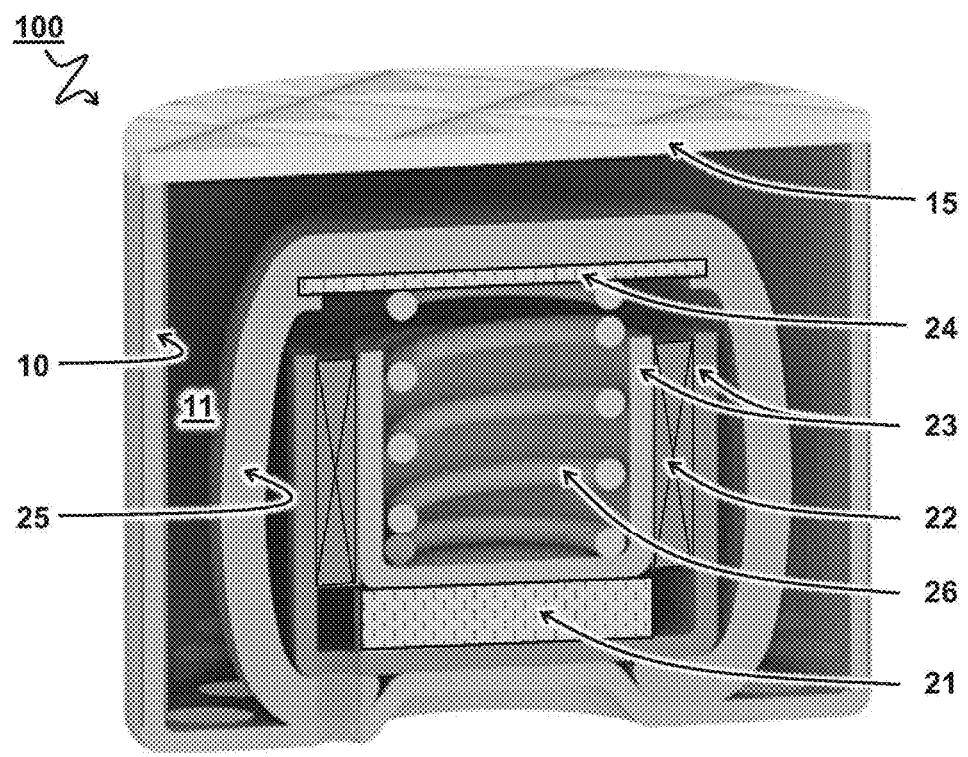
FIGS. 7A and 7B illustrate acoustic devices including a respective spring mechanism that may increase or decrease a resilient force of the deformable shape
Figure 7B:
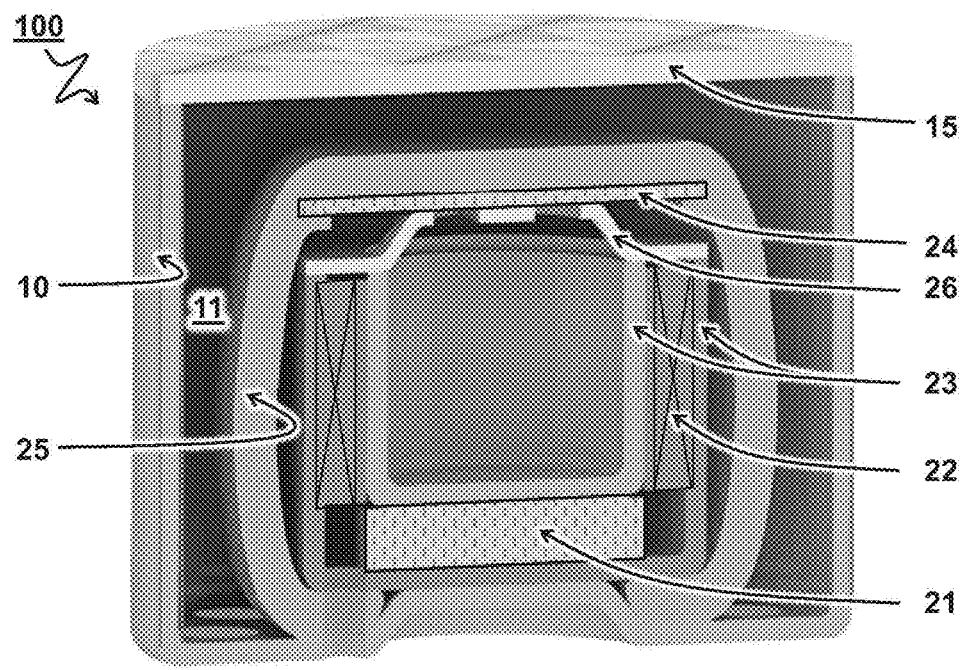
Figure 8A:
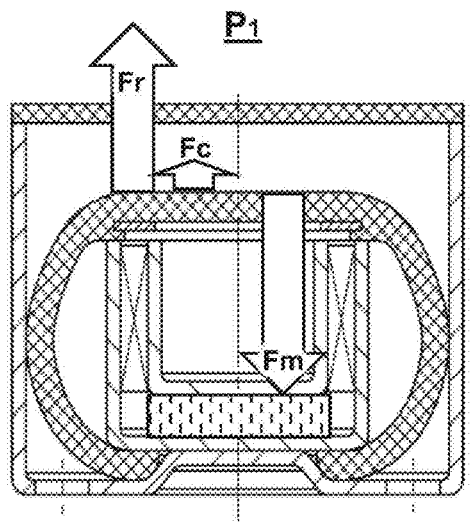
FIGS. 8A-8D illustrate a method of operating an acoustic device as described herein.
Figure 8B:
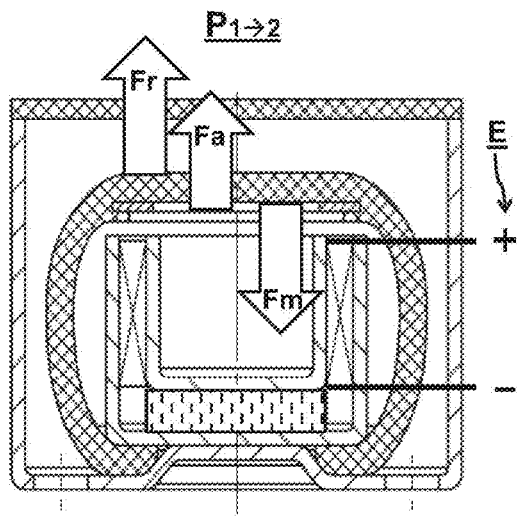
Figure 8C:
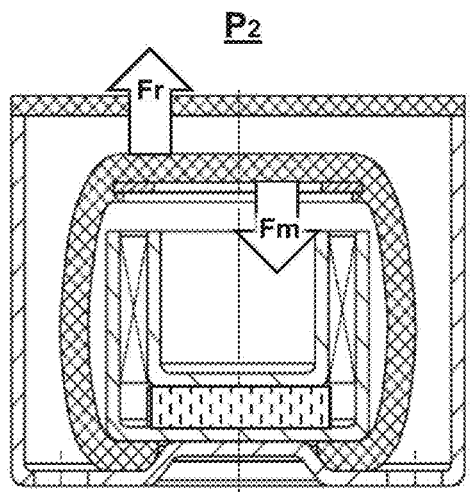
Figure 8D:
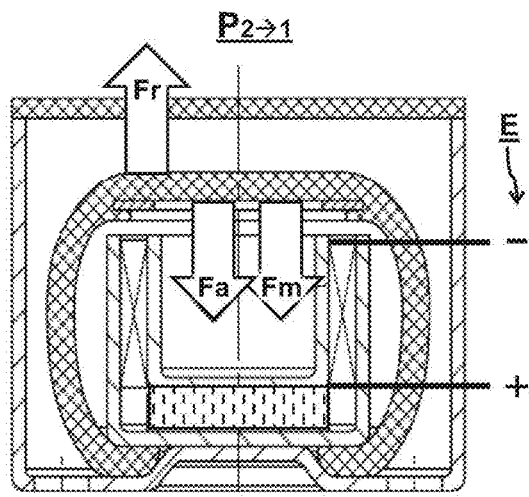

FIGS. 7A and 7B illustrate acoustic devices 100 including a respective spring mechanism 26 which may increase or decrease a resilient force Fr of the deformable shape 25. Preferably, the spring mechanism 26 is biased to partly counteract attraction between the magnetic components. Advantageously, by including an additional spring mechanism 26, the resilient force can be more easily tuned to at least partially counteract magnetic force making it easier to switch the magnets apart. In some embodiments, the spring mechanism can also help to stabilize the position when the magnetic components are apart.

In some illustrative examples, e.g. as shown in FIG. 7A, the acoustic device 100 comprises a coil shaped spring mechanism 26, disposed inside the electromagnetic coil 22, e.g. inside the cup shaped yoke material 23. In other or further illustrative examples (not shown), the spring mechanism 26 can also be disposed around the outside of the electromagnetic coil 22, e.g. around the outer cup of yoke material 23. In other or further examples, e.g. as shown in FIG. 7B, the acoustic device 100 comprises a leaf spring mechanism 26, advantageously disposed between the electromagnetic coil 22 and the moveable magnetizable material 24 (or moveable permanent magnet).

FIGS. 8A-8D illustratively depict a method of operating an acoustic device 100 as described herein. In an illustrative example, the method comprises energizing the actuating mechanism 20a to switch between a first state P1 wherein the deformable shape 25 blocks the acoustic channel 11 to restrict the passage of sound S; and a second state P2 wherein the deformable shape 25 clears the acoustic channel 11 to allow the passage of sound S. Typically, the energizing comprises generating an electric current E through a wiring of an electromagnetic coil to generate an actuating force Fa by a magnetic field generated by the coil. In some illustrative examples, a direction of the current, or polarity, can be used to either counteract or enhance the magnetic force Fm of the permanent magnet and/or the resilient force Fr of the deformable shape (and/or spring mechanism).

Figure 9:
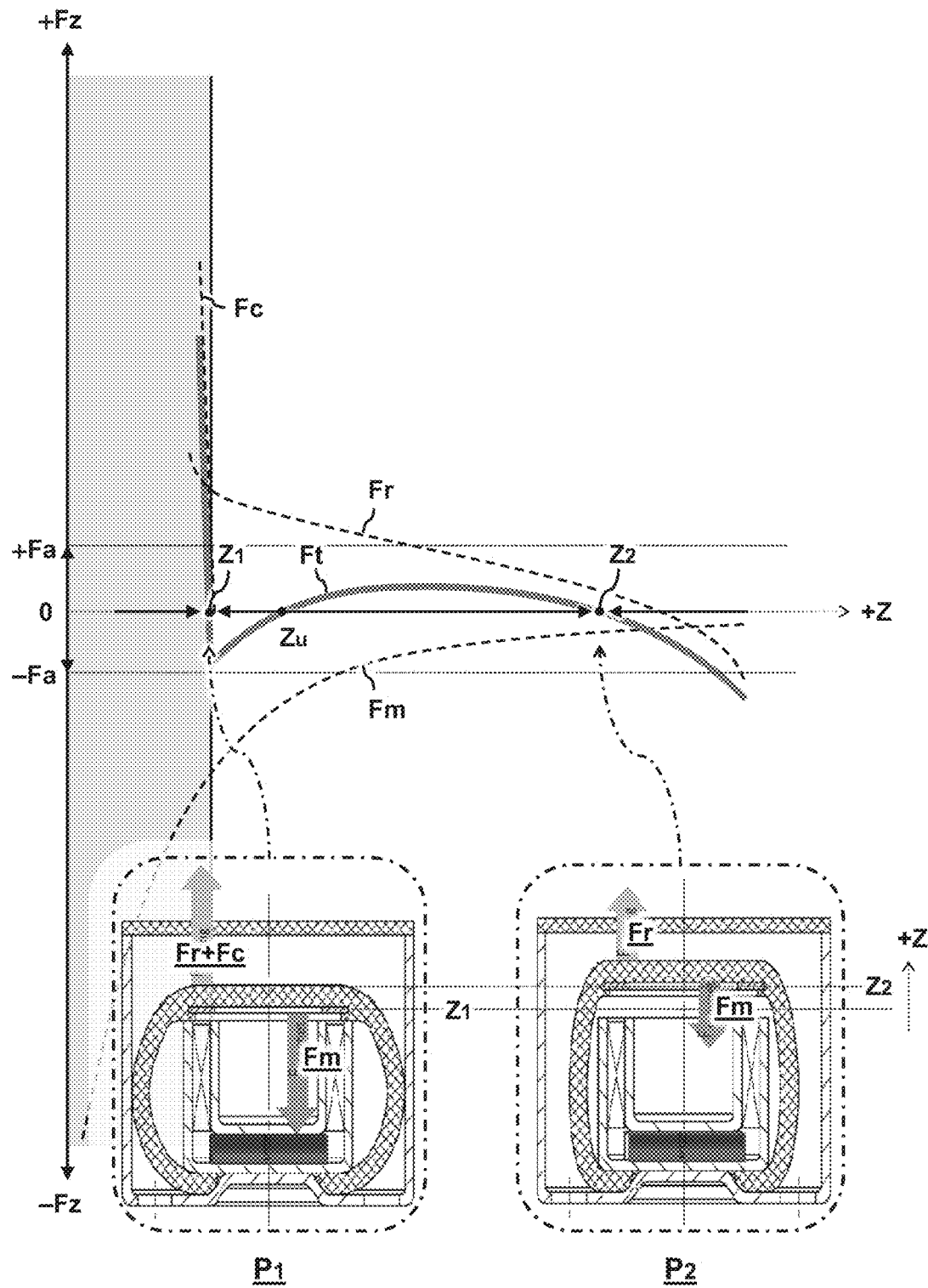
FIG. 9 illustrates a graph of various forces as function of axial displacement.

FIG. 9 illustratively depicts a graph of various forces F as a function of axial displacement Z. The graph indicates relative magnitude and direction of the forces wherein positive values correspond to a repellent force +Fz moving the magnetic components apart in the +Z direction; and negative values correspond to an attractive force −Fz moving the magnetic components together in the −Z direction.

The illustrated graph includes an example of the magnetic force Fm, which can be attributed to the permanent magnet. Typically, the magnetic force decreases non-linearly, e.g. as the square or cube of the distance (depending on approximation, e.g. determined by the extent, shape and relative distance between magnetic parts). Accordingly, the magnetic force Fm can be relatively high when the magnetic components are close together and rapidly decrease for increasing distance.

The depicted graph includes an example of the resilient force Fr, which can be attributed to resilience of the deformable shape, optionally in combination with the spring mechanism. Typically, the resilient force Fr can be relatively linear, at least within a certain range, e.g. until the deformable shape starts to abut the side walls of the housing or gets overextended. The graph can be more linear when using the optional spring mechanism in its linear range. As will be appreciated, the resilient force Fr may also cross zero, at which point the force can start to act in the opposite direction.

The depicted illustrative graph includes an example of a contact force Fc, which can be attributed to the contact between the moveable and stationary components of the actuating mechanism. As shown, the contact force Fc can quickly increase to stop the moveable component against the stationary surface.

Advantageously, the resilient force Fr of the deformable shape 25, and optional spring mechanism 26, is tuned in relation to the magnetic force Fm of the permanent magnet 21 such that at least one stable position is obtained. In particular, opposing forces may cancel out at specific positions, so that the total force Ft is zero and a stable state can be formed. In the illustrated graph, stable positions are formed at Z1 and Z2.

In an illustrative example, the acoustic valve is held in a first stable position Z1 by a magnetic force Fm of a permanent magnet 21, and the valve is held in a second stable position Z2 by a resilient force Fr working against the magnetic force Fm; wherein the actuating mechanism 20a is configured to move the valve between the stable positions Z1,Z2 by overcoming either the magnetic or resilient force.

At a first position Z1, the magnetic force magnetic force Fm can be greater than the resilient force Fr, but the difference can be cancelled by the contact force Fc of contacting surfaces. As a unique feature of embodiments described herein, it is in principle not necessary to provide a second contacting surface (at least not opposing the first contact surface) to get a second stable position Z2, as this can be achieved at the point where any residual magnetic force Fm is cancelled by the resilient force Fr (or the resilient force is also zero). It is noted that the total force is also zero at position Zu, but this is typically an unstable equilibrium because the forces on either side of this point are in opposite directions (like a peak or saddle point)

In an illustrative example, in the first stable position Z1, the sum of the resilient and magnetic forces Fr+Fm is equal and opposite to a contact force Fc of the actuated perimeter 25z of the deformable shape 25 abutting a valve seat. In another or further illustrative example, in the second stable position Z2, the sum of the resilient and magnetic forces Fr+Fm is zero (without abutting a second valve seat opposite the first valve seat). Without being bound by theory, an advantage of not requiring a second valve seat may include a reduction of the force to move the valve. For example, when the valve is forced against a valve seat, this typically implies there is some extra residual force pushing the valve against the seat. This extra force, e.g. excessive resilient force Fr needs to be overcome when switching back the valve, which can cost more energy.

Figure 10A:
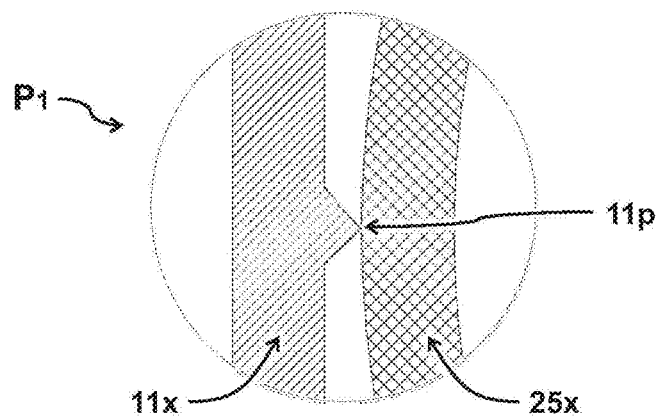
FIGS. 10A-10C illustrate various contact surfaces between the deformable perimeter of the deformable shape and the (relatively rigid) opposing wall of the acoustic channel.
Figure 10B:
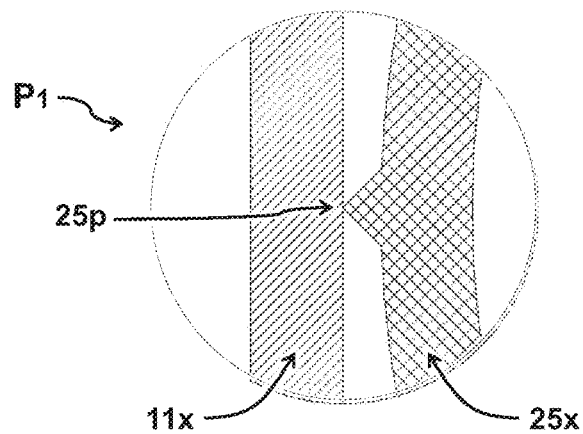
Figure 10C:
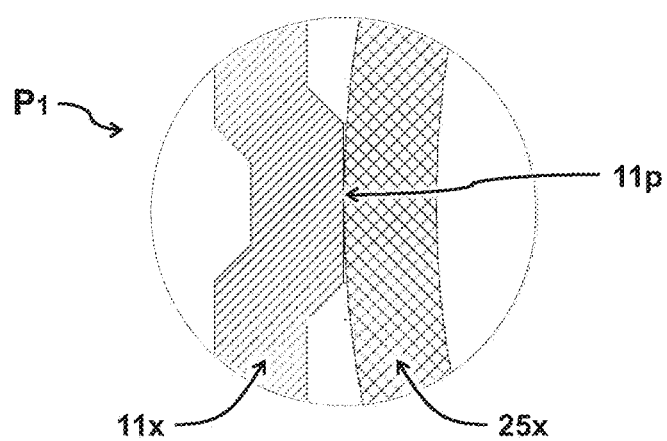

FIGS. 10A-10C illustratively depict various contact surfaces between the deformable perimeter 25x of the deformable shape and the (relatively rigid) opposing wall 11x of the acoustic channel. In an illustrative example, at least one of the deformable perimeter 25x and/or an opposing wall 11x of the acoustic channel 11 comprises a protrusion 25p, 11p to improve sealing of the acoustic channel 11 when the deformable perimeter 25x is moved towards the opposing wall 11x.

In some illustrative examples, e.g. as shown in FIG. 10A, the opposing wall 11x comprises a respective protrusion 11p. For example, the protrusion 11p comprises a rim on a circumference of the opposing wall 11x surrounding the deformable perimeter 25x. In other or further embodiments, e.g. as shown in FIG. 10B, the deformable perimeter 25x comprises a respective protrusion 25p. For example, the protrusion 25p comprises a rim on an outer circumference of the deformable perimeter 25x facing the opposing wall 11x that surrounds the deformable perimeter 25x. In other or further embodiments, e.g. as shown in FIG. 10C, the protrusion 11p on the opposing wall 11x (and/or protrusion on the deformable perimeter 25x) comprises a protruding edge shape, which can form a connection to the opposing perimeter or wall to more effectively close the channel. The protruding rim on the deformable shape 25 or opposing wall 11x may also help to reduce acoustic mass in the open passage.

Figure 11A:
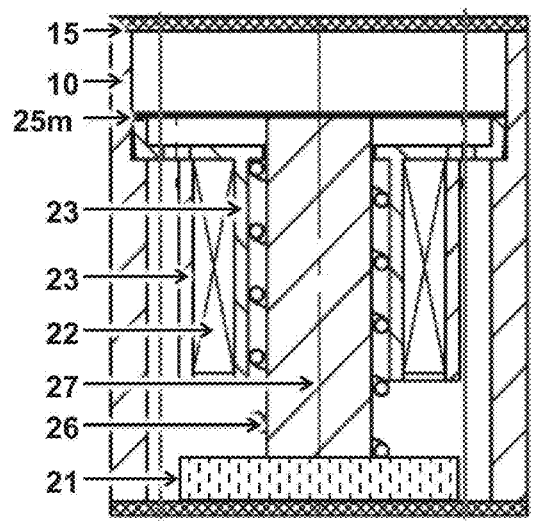
FIGS. 11A-11C illustrates an acoustic device with a stretchable membrane actuated by a moveable piston.
Figure 11B:
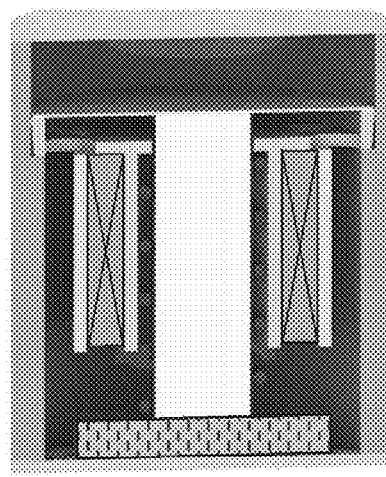
Figure 11C:
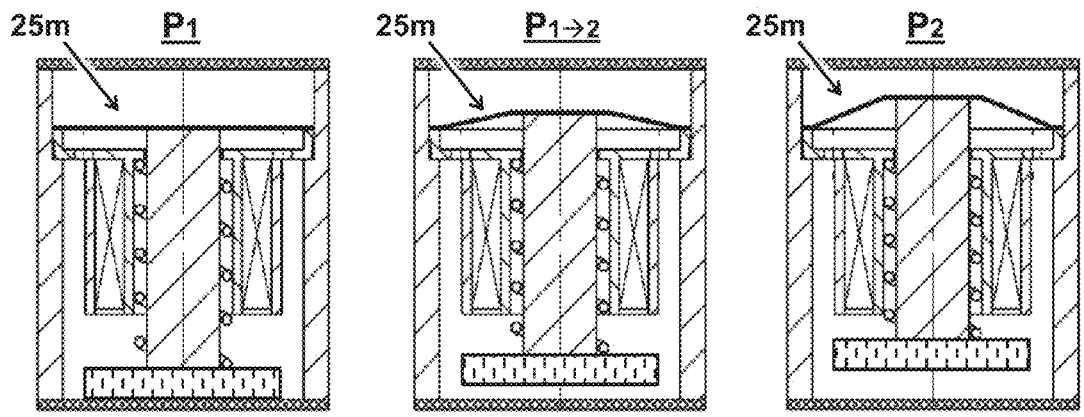

FIGS. 11A-11C illustratively depict an acoustic device 100 with a stretchable membrane 25m actuated by a moveable piston 27. In some acoustic devices, e.g. as shown, a permanent magnet 21 is directly or indirectly attached to stretchable membrane 25m that can be stretched by a piston there between. For example, the passage of sound can be determined by a degree of stretching of the membrane 25m. The membrane may thus act similarly as the deformable shape. In one position P1, the membrane can be relatively unstretched (although it can be pre-stretched mounted). In another position P2, the membrane can be more stretched. For example, the membrane can pass a different sound characteristic when it is more stretched.

Figure 12A:
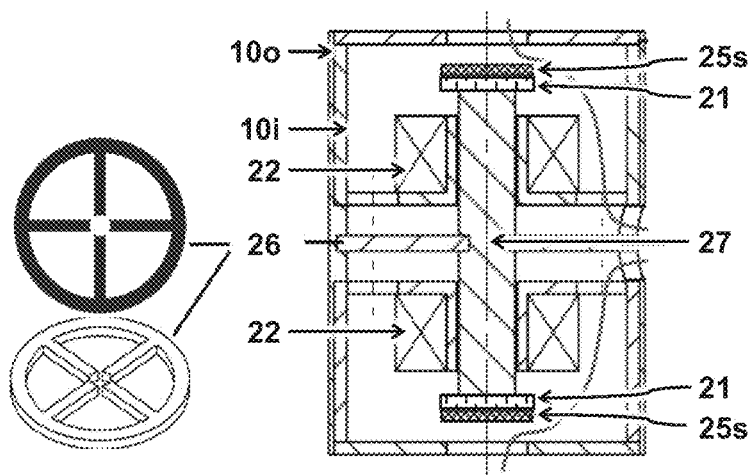
FIGS. 12A-12C illustrates another acoustic device with a moveable piston.
Figure 12B:
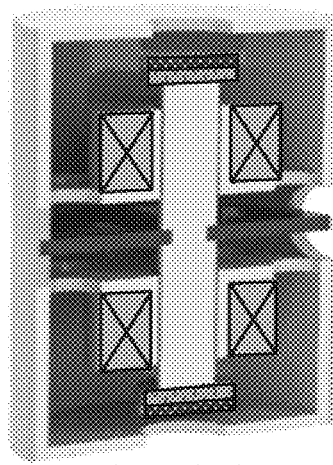
Figure 12C:
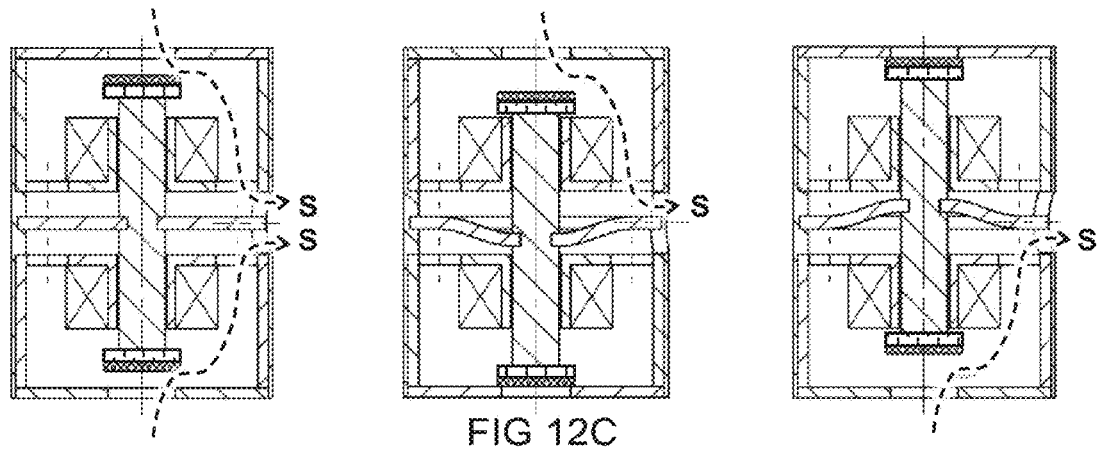

FIGS. 12A-12C illustratively depict another acoustic device 100 with a moveable piston. In some acoustic devices, e.g. as shown, a piston 27 can be used to connect different permanent magnets 21 so the device. For example, this may allow the device to switch between more than two positions. While the present figure shows a device wherein sealing material 25s is actuated to open or close a passage, the material can also be extended, e.g. surrounding the actuating mechanism to form a shell or bubble around the electromagnetic coil 22 (not shown), like described before.

Figure 13A:
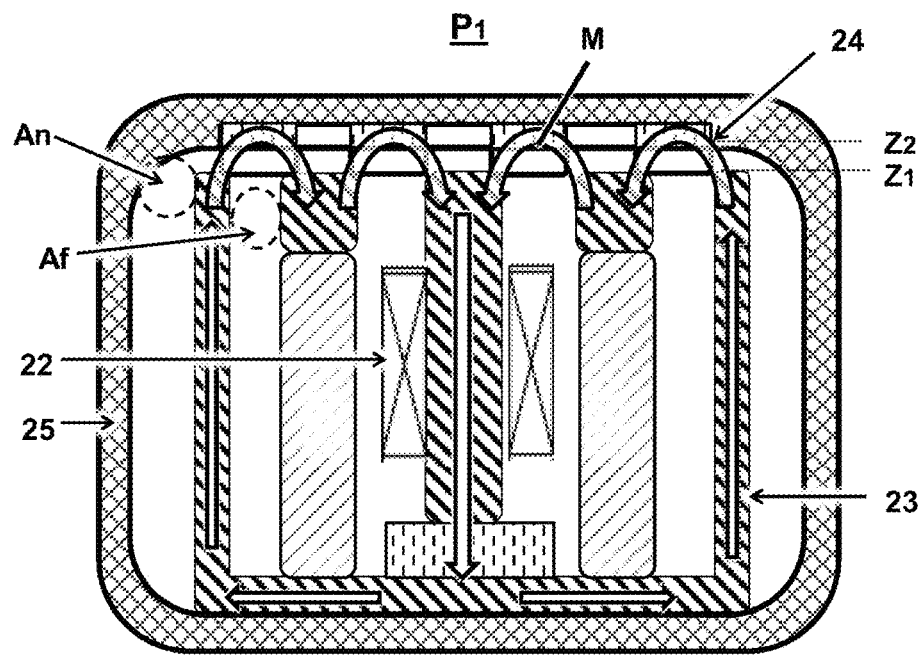
FIGS. 13A and 13B illustrate an acoustic device comprising magnetisable material in series.
Figure 13B:
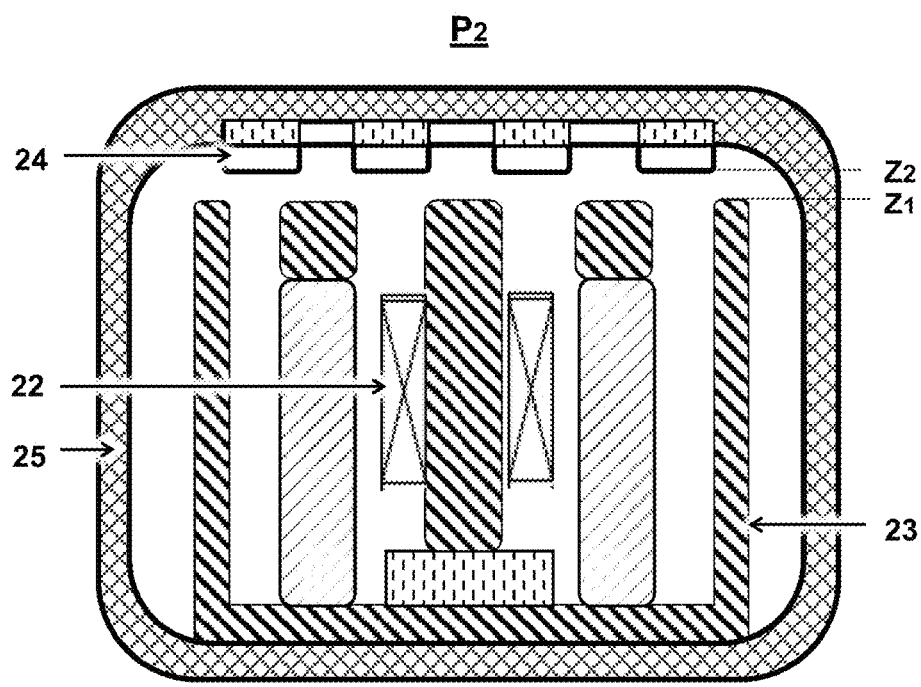

FIGS. 13A and 13B illustratively depict an acoustic device comprising magnetic or magnetizable material 24 in series to open or close a magnetic circuit M. As shown, the material can be split up across multiple (functional) air gaps Af. This may be contrasted with the airgaps An that may have other functions instead of closing the magnetic circuit. By splitting the magnetic or yoke material across multiple air gaps to open/close the magnetic circuit this may further improve closure and the opening forces with respect to the deformable shape 25.

Figure 14A:
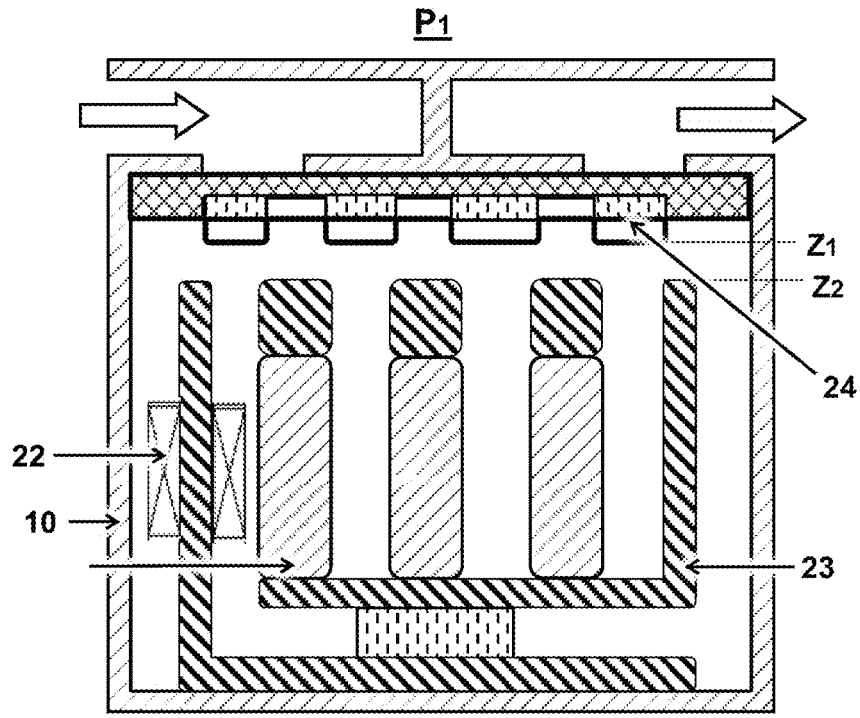
FIGS. 14A and 14B illustrate an acoustic device with an upper audio channel.
Figure 14B:
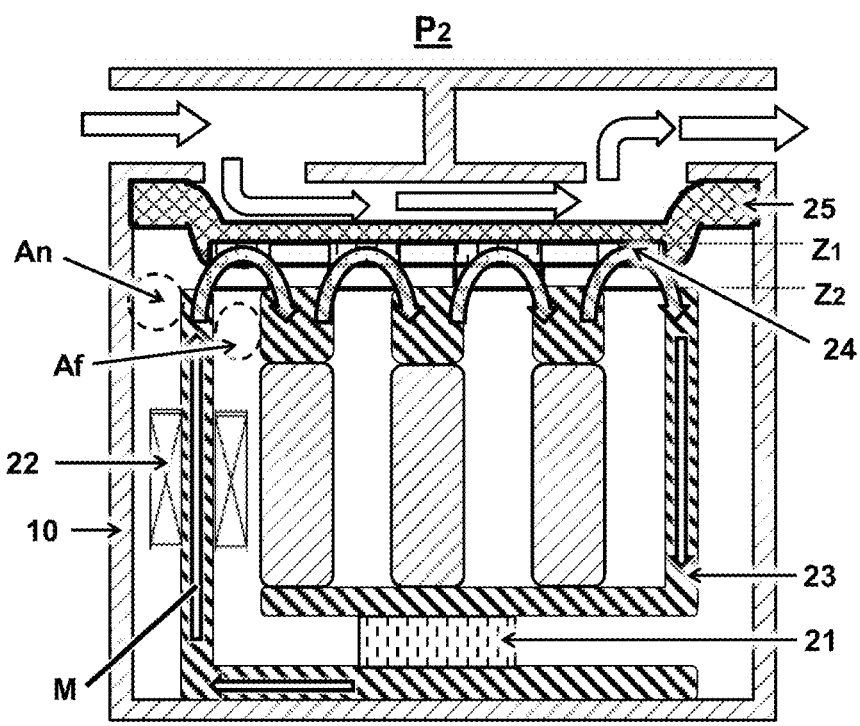

FIGS. 14A and 14B illustratively depict an acoustic device with an upper audio channel. For example, the channel can be in an open position P2 when the magnetic circuit M is closed, and closed otherwise. As also illustrated here, the electromagnetic coil 22 can in principle be placed anywhere along the magnetic circuit M.

For the purpose of clarity and a concise description, features are described herein as part of the same or separate embodiments, however, it will be appreciated that the scope of the invention may include embodiments having combinations of all or some of the features described. In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. Where one claim refers to another claim, this may indicate synergetic advantage achieved by the combination of their respective features. But the mere fact that certain measures are recited in mutually different claims does not indicate that a combination of these measures cannot also be used to advantage. The present embodiments may thus include all working combinations of the claims wherein each claim can in principle refer to any preceding claim unless clearly excluded by context.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Illustrative examples of this invention are described herein, including the best mode known to the inventors for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An acoustic device comprising:
   a housing;
   an acoustic channel extending through the housing; and
   an acoustic valve disposed in the acoustic channel and configured to determine a passage of sound through the housing via the acoustic channel, wherein the acoustic valve comprises:
      a deformable shape forming a deformable perimeter of the acoustic channel, and
      an actuating mechanism configured to exert an actuating force deforming the deformable shape causing the deformable perimeter to move and change the passage of sound;
   wherein the deformable shape is shaped as a dome or bubble configured to act as a barrier sealing the actuating mechanism from an inside of the acoustic channel, and
   wherein the actuating mechanism is configured to exert the actuating force in an axial direction, from inside the dome or bubble, causing the dome or bubble to expand or contract the deformable perimeter in a radial direction, around and transverse to the axial direction.

2. The acoustic device according to claim 1, wherein the actuating mechanism is configured to change, by moving the deformable perimeter in the acoustic channel, a state of the acoustic device between:
   a first state wherein the passage of sound is relatively restricted, and
   a second state wherein the passage of sound is relatively open.

3. The acoustic device according to claim 1, wherein the actuating mechanism is configured to exert the actuating force on the deformable shape causing the deformable perimeter to expand into, or retract from, the acoustic channel to thereby at least partially close, or open up, the passage of sound through the acoustic channel.

4. The acoustic device according to claim 1, wherein the actuating mechanism is configured to exert an actuating force on the deformable shape in a first direction causing the deformable shape to deform in another, second direction for changing the passage of sound.

5. The acoustic device according to claim 1, wherein the deformable shape comprises a flexible shell of deformable material.

6. The acoustic device according to claim 1, wherein the deformable shape is rotationally symmetric about the axial direction, wherein the actuating mechanism is configured to actuate a proximal perimeter of the deformable shape to move along the axial direction, causing expansion or contraction of the deformable perimeter in the radial direction.

7. The acoustic device according to claim 1, wherein the deformable shape comprises an elastically deformable material configured to exert a restoring, resilient force when deformed.

8. The acoustic device according to claim 1, wherein the actuating mechanism comprises:
a moveable magnet or magnetizable piece of material attached to a proximal side of the deformable shape, and
an electromagnet configured to generate the actuating force by generating a magnetic field acting on the moveable magnet or magnetizable piece of material.

9. The acoustic device according to claim 1, wherein a stationary permanent magnet is disposed between inner and outer yoke material inside and outside an electromagnetic coil, wherein a moveable permanent magnet or magnetizable material attached to the deformable shape is configured to complete the magnetic circuit and maintain the connection also in the absence of an electrical current through the electromagnetic coil.

10. The acoustic device according to claim 1, comprising:
a permanent magnet, and
a spring mechanism to increase or decrease a resilient force of the deformable shape counteracting a magnetic force of the permanent magnet.

11. The acoustic device according to claim 1, wherein the acoustic valve is held in a first stable position by a magnetic force of a permanent magnet,
wherein the valve is held in a second stable position by a resilient force working against the magnetic force,
wherein the actuating mechanism is configured to move the valve between the first and second stable positions by overcoming either the magnetic force or the resilient force,
wherein in the first stable position the sum of the resilient and magnetic forces is equal and opposite a contact force of an actuated perimeter of the deformable shape abutting a valve seat, and
wherein in the second stable position the sum of the resilient and magnetic forces is zero.

12. The acoustic device according to claim 1, wherein at least one of the deformable perimeter and/or an opposing wall of the acoustic channel comprises a protrusion to improve sealing of the acoustic channel when the deformable perimeter is moved towards the opposing wall.

13. A method of controlling an acoustic valve disposed in an acoustic channel through a housing of an acoustic device to determine a passage of sound through the housing via the acoustic channel, wherein the acoustic valve comprises a deformable shape forming a deformable perimeter of the acoustic channel, and an actuating mechanism configured to exert an actuating force deforming the deformable shape causing the deformable perimeter to move and change the passage of sound;
the method comprising energizing the actuating mechanism to switch between:
a first state wherein the deformable shape at least partially blocks the acoustic channel to restrict the passage of sound; and
a second state wherein the deformable shape at least partially clears the acoustic channel to allow the passage of sound
wherein the deformable shape is shaped as a dome or bubble configured to act as a barrier sealing the actuating mechanism from an inside of the acoustic channel, and
wherein the actuating mechanism is configured to exert the actuating force in an axial direction, from inside the dome or bubble, causing the dome or bubble to expand or contract the deformable perimeter in a radial direction, around and transverse to the axial direction.

14. The method of claim 13, wherein a stationary permanent magnet is disposed between an inner and an outer yoke material inside and outside an electromagnetic coil, wherein a moveable permanent magnet or magnetizable material attached to the deformable shape is configured to complete the magnetic circuit and maintain the connection also in the absence of current through the electromagnetic coil.

15. The method of claim 13, wherein the acoustic valve comprises a permanent magnet, and a spring mechanism to increase or decrease a resilient force of the deformable shape counteracting a magnetic force of the permanent magnet.

16. The method of claim 13, wherein the acoustic valve is held in a first stable position by a magnetic force of a permanent magnet, and the valve is held in a second stable position by a resilient force working against the magnetic force,
wherein the actuating mechanism is configured to move the valve between the first and the second stable positions overcoming either the magnetic or resilient force,
wherein in the first stable position the sum of the resilient and magnetic forces is equal and opposite a contact force of an actuated perimeter of the deformable shape abutting a valve seat, and
wherein in the second stable position the sum of the resilient and magnetic forces is zero.

* * * * *